United States Patent [19]

Caspi

[11] Patent Number: 5,422,270
[45] Date of Patent: Jun. 6, 1995

[54] ONE-STEP TRAY TEST FOR RELEASE OF SOLUBLE MEDIATORS AND APPARATUS THEREFORE

[75] Inventor: Rachel R. Caspi, Bethesda, Md.

[73] Assignee: The United States of America as represented by the Department of Health and Human Services, Washington, D.C.

[21] Appl. No.: 51,313

[22] Filed: May 19, 1987

[51] Int. Cl.⁶ .................. C12M 3/00; C12M 3/04
[52] U.S. Cl. .................. 435/284; 435/299; 435/287; 435/300; 435/6; 435/33; 435/819; 435/973; 435/286
[58] Field of Search .............. 435/300, 287, 240.1, 435/284; 436/809; 422/99; 356/244; 424/9

[56] References Cited

U.S. PATENT DOCUMENTS

| | | | |
|---|---|---|---|
| 3,272,719 | 9/1966 | Avakian | 435/301 |
| 3,649,464 | 3/1972 | Freeman | 435/284 |
| 3,938,961 | 2/1976 | Lanier | 422/102 |
| 4,012,198 | 3/1977 | Finter et al. | 422/56 |
| 4,120,119 | 10/1978 | Engel | 47/66 |
| 4,154,795 | 5/1979 | Thorne | 422/99 |
| 4,241,187 | 12/1980 | White | 435/284 |
| 4,246,339 | 1/1981 | Cole et al. | 435/5 |
| 4,537,860 | 8/1985 | Tolbert et al. | 435/240.241 |
| 4,599,315 | 7/1986 | Terasaki et al. | 435/301 |
| 4,665,034 | 5/1987 | Chandler | 435/287 |
| 4,962,855 | 10/1990 | Holmquist | 206/423 |
| 5,022,183 | 6/1991 | Bohlmann | 47/86 |

FOREIGN PATENT DOCUMENTS

| | | |
|---|---|---|
| 0121981 | 10/1984 | European Pat. Off. |
| 0199205 | 10/1986 | European Pat. Off. |
| 0290018 | 11/1988 | European Pat. Off. |
| 2094831 | 9/1982 | United Kingdom |
| 2733705 | 6/1970 | U.S.S.R. |

OTHER PUBLICATIONS

VWR Catalog 1987–1988, pp. 582 & 580.
Noggle et al. 1976, In: *Introductory Plant Physiology*, Prentice-Hall, Inc. N.J., pp. 307–316.
Curtis H. 1975, In: *Biology*, Second Edition, Worth Publishers, Inc. p. 50.
Hackh's Chemical Dictionary 1969, (Grant, ed.), McGraw-Hill Book Co. p. 334.
Webster's II New Riverside Dictionary, 1984, The Riverside Publ. Co., Mass. p. 601.
Fresney, R. I. 1983, In: *Culture & Animal Cells, A Manual of Basic Technique*, Alan R. Liss, Inc. NY, p. 55.
Avakian, US,3,272,719 (enlarged figure).
Webster's II, New Riverside Dictionary, 1984, The Riverside Publ. Co., Mass. pp. 852, and 1306.
Little et al, 1986, Corrosion, 42, 533–536.
Caspi, "A rapid one-step multiwell tray test for release of soluble mediators", Journal of Immunol. Methods, 93 (1986) 141–144.
Caspi et al, Organ-Resident, Nonlyphoid Cells Suppress Proliferation of Autoimmune T–Helper Lymphocyters, Aug. 23, 1987, vol. 237, pp. 1029–1032.
Caspi et al, Characterization of a Suppressor Cell Line Which Downgrades Experimental Autoimmune Uveoretinitis in the Rat, Journal of Immunol., vol. 140, 2579–2584, No. 8, Apr. 15, 1988.

*Primary Examiner*—Christopher S. F. Low
*Attorney, Agent, or Firm*—Lowe, Price, LeBlanc & Becker

[57] ABSTRACT

A microculture tray comprising a plurality of pairs of wells, each pair of wells connected by a trough which extends downwardly approximately ⅔ of the depth of the well so that the wells in the pair are connected so as to allow free passage of supernatant but not of cells between the wells.

The tray can be used for rapid testing of animal cells or non-motile microorganisms for the release of soluble mediators.

6 Claims, 2 Drawing Sheets

ONE-STEP TRAY TEST FOR RELEASE OF SOLUBLE MEDIATORS AND APPARATUS THEREFORE

FIELD OF THE INVENTION

The present invention relates to a method and apparatus for detecting rapid release of soluble mediators from cultured cells.

BACKGROUND OF THE INVENTION

Testing for the release of soluble mediators is customarily performed by collecting the supernatant of the cells which release the putative substance, and adding this substance to cultures of indicator cells, the growth of which can be measured by $^3$H-thymidine uptake. This procedure takes several days, and some short-lived mediators, such as prostaglandins, may not be measurable in this way, as they would deteriorate in the medium. Labile substances may be bioassayed in a one-step procedure, by plating the producer and the indicator cultures in chambers separated by a semipermeable membrane, such as the Marbrook chamber, through which the soluble substance can diffuse as it is produced. This chamber is described in greater detail in Marbrook, J., 1980, in Selected Methodsin Cellular Immunology, eds. B. B. Mishell and S. M. Shiigi (W. H. Freeman and Company, San Francisco) p.37. The drawback of this method is that some mediators may bind to the membrane, and that standard cell labelling and harvesting procedures cannot be used directly to assay the growth of the indicator culture.

In British patent No. 2,094,831 A, there is described a tray for identifying isolated microorganisms consisting of a plastic or glass tray body and a cover. Each cell in the tray has a barrier which is nearly vertical on one side and sloping on the other, the barrier being lower in height that the overall cell walls. In use, dried reagents are prepared in the wells of the small cells, bacterial suspension is poured into each of the adjoining cells, and the entire tray is inclined so that the cells for bacterial suspension are introduced over the barriers to inoculate the reagent cells.

European Patent No. 121,981, discloses a support for an immobilized cell composite. The support structure is a honeycombed monolith having inlet and outlet faces which allow liquid to flow through channels in the monolith to provide nutrients to the anchored cells.

Tolbert et al., U.S. Pat. No. 4,537,860, disclose an apparatus for maintaining animal cells in vitro in a substantially arrested state of proliferation with continuous secretion of cell product. The cells are retained in the reactor vessel chamber in a semirigid matrix having interstices for passage of fluid nutrient medium.

Lanier, U.S. Pat. No. 3,938,961 discloses a sample tray for storing fluid test specimens suitable for filling fluid dispensers. Isolated catch basins surround each test specimen reservoir so as to prevent commingling of test specimen fluids that may spill over the edge of the fluid receiving compartment, either during filling or while the specimen fluid is being withdrawn therefrom.

SUMMARY OF THE INVENTION

It is an object of the present invention to overcome the deficiencies in the prior art, as outlined above.

It is a further object of the present invention to provide a method for testing for the release of soluble mediators.

It is yet a further object of the present invention to provide apparatus to provide for rapid testing of animal cells or non-motile microorganisms for the release of soluble mediators.

It is yet another object of the present invention to provide a tissue culture tray having a plurality of wells for rapid testing of animal cells or non-motile microorganisms for the release of soluble mediators.

According to the present invention, culture of cells and determination of the release of soluble mediators is accomplished in a tissue culture tray having a plurality of wells wherein adjacent pairs of wells in the tray are connected to each other in such a fashion as to allow free passage of the supernatant but not of cells between the cultures. It has been found that the wells are conveniently connected by troughs which extend downwardly approximately ⅔ of the depth of the well from the top.

DETAILED DESCRIPTION OF THE INVENTION

Figure 1:
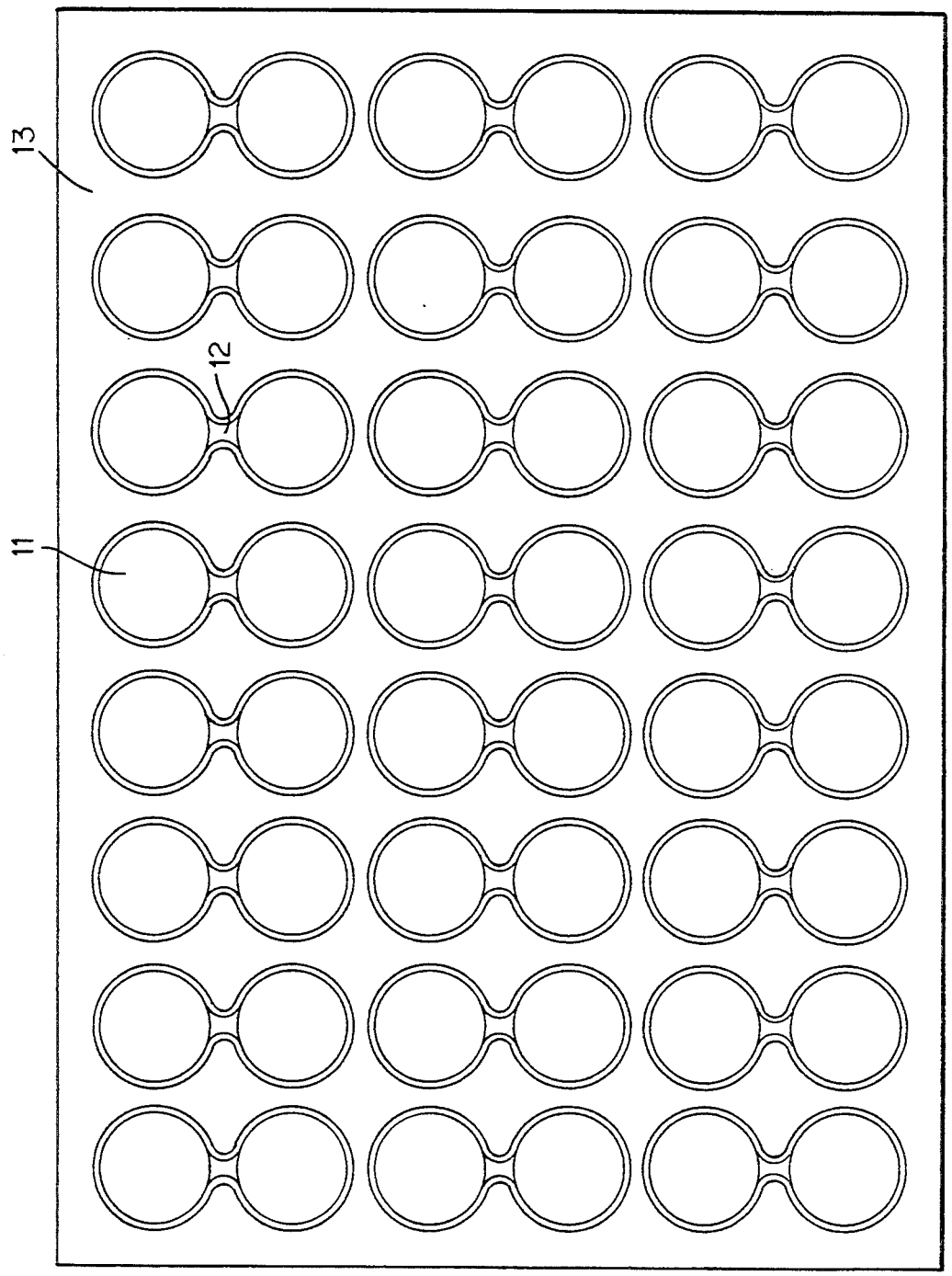
FIG. 1 shows a microculture tray according to the present invention.

A. In one specific application of the process and apparatus of the present invention, the release of a putative lymphocyte growth inhibitor by cultured glial cells (Muller cells) was measured. The activity of this lymphocyte growth inhibitor could not be detected by transfer of Muller cell culture supernatants onto cultures of the target ThS lymphocytes. By using the present invention it was shown that this putative growth inhibitor is a cell-bound, rather than a soluble, substance (Table 1).

TABLE 1

REQUIREMENT FOR CONTACT BETWEEN T-HELPER CELLS (ThS) AND MÜLLER CELLS (Mu) FOR EFFECTIVE INHIBITION OF ThS PROLIFERATION

| CULTURE | CPM × 10$^{-3}$ $^3$H-TdR | |
|---|---|---|
| | +S-Antigen | no stimulant |
| none | — | — |
| ‖ | | |
| ThS/APC | 59.3 | 0.1 |
| Mu | 3.9 | 3.7 |
| ‖ | | |
| ThS/APC | 44.5 | 0.1 |
| none | — | — |
| ‖ | | |
| Mu/ThS/APC | 5.3 | 3.8 |
| ThS/APC | 42.8 | 0.1 |
| ‖ | | |
| Mu/ThS/APC | 3.3 | 3.6 |

The specified cultures were seeded in each of quadruplicate 0.2 ml connected wells, in a modified 96-well culture tray. The "‖" symbol denotes the communicating cultures. Each 0.2 ml well contained 2 × 10$^4$ ThS (+4 × 10$^6$ APC) and 1 × 10$^4$ Müller cells (3000 R), individually or in co-culture. After allowing the cells to settle for 2 hours, supernatants of the paired cultures were brought into contact and the antigen was added in a volume of 10 μl to the specified cultures, to the final concentration of 10 μg/ml. The cultures were incubated for 60 h and were pulsed with 1 μCi $^3$H-TdR/well for the last 14 h. Standard errors were <10% of the mean.

According to the present invention, the two types of cells to be cultured were cultured in connected adjacent pairs of wells of a 96-well tissue cultures tray. The tissue culture tray was configured so as to allow free passage of the supernatant, but not of the cells, between the 5 cultures. At the end of the incubation period the cultures were labelled in situ with $^3$H-thymidine ($^3$H-TdR) and harvested by using a standard automatic cell harvester.

In order to differentiate between suppression by a labile inhibitory factor and suppression mediated by direct contact, a one-step assay system employing directly communicating cultures of Muller and T-helper cells was designed. The method is based on plating the producer and the responder cultures in connected adjacent wells of the modified 96-well tissue culture tray according to the present invention, so as to allow free passage of the culture supernatant, but not of the cells, between the communicating wells. This method obviates the use of a semimpermeable membrane between the cultures, thus eliminating the possibility that a putative inhibitor might be binding to the membrane, and allows labeling and harvesting of replicate cultures in the usual way. The results of this assay clearly showed that the Muller and the T-helper cells must reside in the same well in order for the suppression to be effective, as shown in Table 1. Even in cultures where one of the paired wells contained both helper and Muller cells and the other helper cells alone (with APC and antigen added to both), the inhibition affected those T-helper cells which were in physical contact with the Muller cells, arguing against the possibility that contact with the helper cells might be inducing production of a soluble mediator of suppression.

B. In another application, the release of soluble mediators that promote the growth of cells (interleukin 2:IL-2, and interleukin 3:IL-3) was measured (R. R. Caspi, 1986 J. Immunol. Meth., 93, 141).

The cells used were as follows:
IL-2 producers:
  a. ThS, a rat T-helper lymphocyte line specific to the retinal soluble antigen (S-Ag), stimulated with S-Ag presented on syngeneic antigen-presenting cells (APC: thymocytes, irradiated 3000R);
  b. IL-2-producing EL-4 mouse thymoma subline (cf. Farrar et al, 1980, J. Immunology 125, 2555), stimulated with phorbol myristic acetate (PMA; Sigma, 5 ng/ml).

The IL-2-dependent indicator cells were a cloned mouse CTLL line.

The IL-3 producers were as follows:
  a. the ThS lymphocyte line, stimulated with S-Ag;
  b. the myelomonocytic WEHI-3 cell line (cf. Lee et al., 1982, J; Immunol. 125, 2184).

The IL-3-dependent DA-1 cell line developed by J. Ihle, FCRF, NIH, was used as indicator cells for the bioassay, as described by Ythier et al., 1985, Proc. Nat. Acad. Sci. 82, 7020.

All cultures were plated in quadruplicate, at the specified number of cells per well, in RPMI 1640 medium (GIBCO) supplemented as previously described, and containing 10% fetal calf serum (Hyclone, Logan, Utah).

Figure 2:
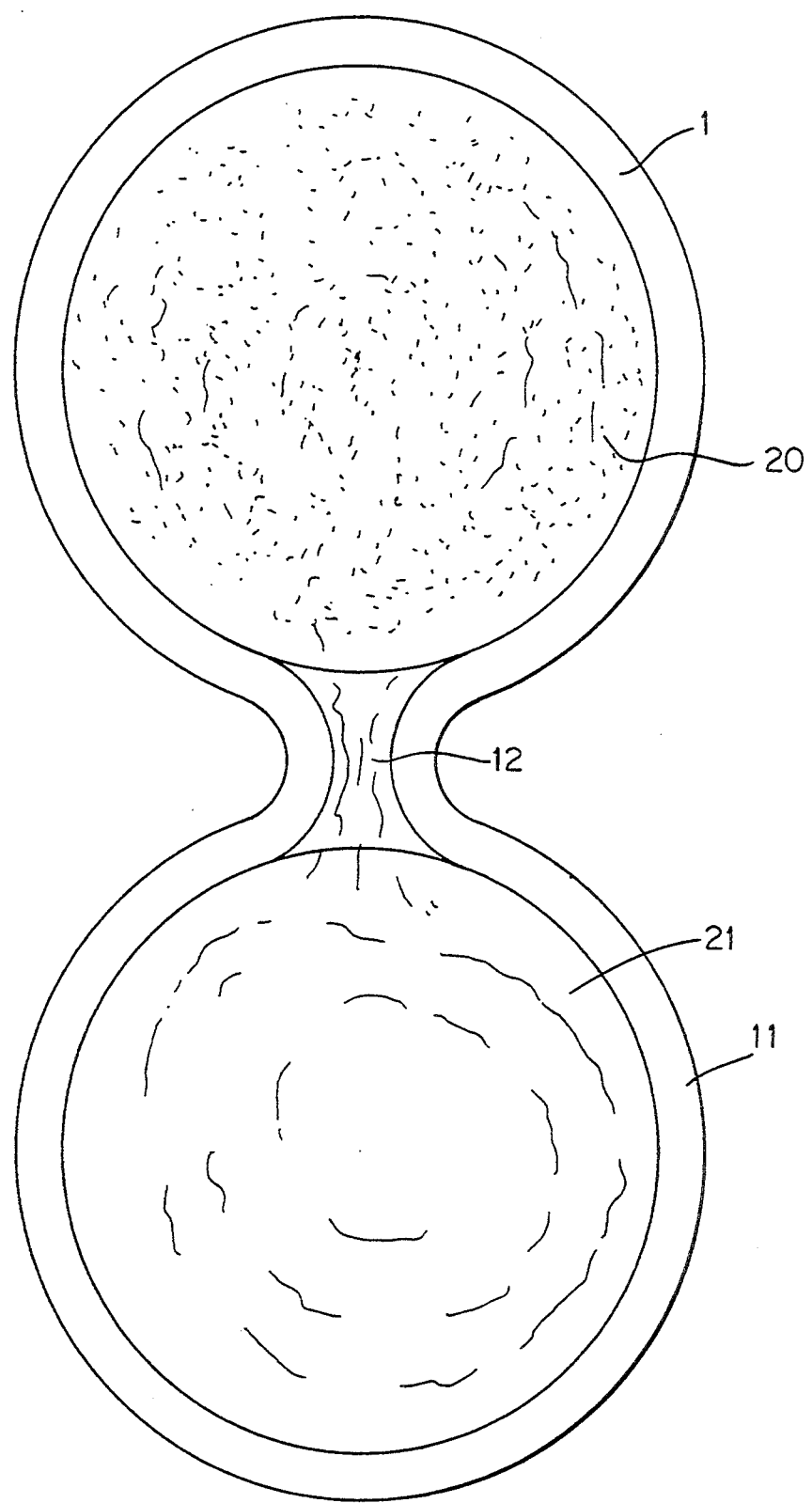
FIG. 2 shows the lack of passage of cells into an adjacent unseeded well.

The dripping method routinely used for regular 96-well tray cultures was used for distributing the cell suspension into the connected wells. Two-ml disposable plastic pipets (Falcon) were connected to an electric pipetting device (Pipet-Aid, Falcon). Two drops from a vertically held pipet equal 0.1 ml. It was found that, whatever method was used to distribute the cells, it is important to keep from wetting the trough between the wells, and thus forming a junction between the two cultures before the cells have had a chance to settle. Because the plastic cultureware is hydrophobic, there was no problem of spontaneous spillage into the connected adjacent well. After careful topping up of the wells, the supernatants of the paired cultures were brought into contact by passing a hypodermic needle through the supernatants at the opening of each well onto the corresponding trough to break the surface tension of the supernatant. This procedure did not disturb the settled cells, as seen by microscopic examination and the lack of passage of the cells into an adjacent unseeded well, as shown in FIG. 2, and by the lack of counts in the control wells in Tables 2 and 3.

The paraffin filling in the interwell spaces other than the troughs did not seem to interfere with cell growth. However, a drop of paraffin inside the well inhibited cell proliferation. Such wells, easily detected by visual inspection of the trays before seeding, were not used. Heating the paraffin before use to about 70° C. for 15–20 minutes was found to be sufficient to ensure sterility.

Harvesting of the cultures was performed without lifting the harvester head during washing, so that mixing of the contents of the connected wells was avoided, as shown by lack of counts in adjacent unseeded wells in the positive control cultures, where the soluble mediator, rather than the producer cells, was added (cf. Tables 2 and 3).

Table 2 shows the assay of IL-2 production in the connected well system according to the present invention. Table 3 shows the assay of IL-3 production in the connected well system according to the present invention.

TABLE 2

ASSAY OF IL-2 PRODUCTION IN THE CONNECTED WELL SYSTEM

The specified number of cells was seeded in each of quadruplicate 0.2 ml connected wells. The " || " symbol denotes the communicating cultures. The cultures were incubated for 24 h and pulsed with 1 μCi $^3$H-TdR/well for 14 h. 1 U of biological activity of IL-2 (supporting 50% maximal proliferation of CTLL) was 40 BRMP U of recombinant human IL-2 (Cetus Corp.) (determined separately). Standard errors did not exceed 10%, and were usually around 5% of the mean.

| | cpm × $10^{-3}$ $^3$H-TdR | |
|---|---|---|
| Cell type (cells/well) | +stimulant[a] | No stimulant |
| ThS/APC(1 × $10^4$) | 46.7 | 0.4 |
| \|\| | | |
| CTLL(5 × $10^3$) | 90.9 | 2.1 |
| EL-4(1 × $10^4$) | 1.4 | 180.8 |
| \|\| | | |
| CTLL(5 × $10^3$) | 65.2 | 4.4 |
| None (control) | 0.4 (2 U IL-2) | 0.2 (medium) |
| \|\| | | |
| CTLL[b](5 × $10^3$) | 90.1 | 0.7 |

[a]Stimulant for ThS: 10 μg/ml S—Ag. Stimulant for EL-4: 5 ng/ml PMA.
[b]CTLL background: with PMA, 8.3 × $10^{-3}$ cpm; with IL-2 plus PMA, 74.5 × $10^{-3}$ cpm.

TABLE 3

ASSAY OF IL-3 PRODUCTION IN THE CONNECTED WELL SYSTEM

The specified number of cells was seeded in each of quadruplicate 0.2 ml connected wells. The " || " symbol denotes the communicating cultures. The cultures were incubated for 24 h and pulsed with 1 μCi $^3$H-TdR/well for 14 h. 1 U of biological activity of IL-3 (supporting 50% maximal proliferation of DA-1) was a 1:200 dilution of a standard preparation of WEHI supernatant (determined previously). N/A: not applicable. Standard errors were less than 10% of the mean.

| Cell type (cells/well) | cpm × $10^{-3}$ $^3$H-TdR | |
|---|---|---|
| | +stimulant[a] | No stimulant |
| ThS/APC(2 × $10^4$) | 75.1 | 0.9 |
| \|\| | | |
| DA-1(5 × $10^3$) | 58.0 | 4.6 |
| ThS/APC(1 × $10^4$) | 43.3 | 0.5 |
| \|\| | | |
| DA-1(5 × $10^3$) | 37.4 | 1.3 |
| WEHI(1 × $10^4$) | | 245.9 |
| \|\| | N/A | |
| DA-1(5 × $10^3$) | | 91.9 |
| None (control) | 0.8 (2 U IL-3) | 0.2(medium) |
| \|\| | | |
| DA-1(5 × $10^3$) | 102.6 | 0.6 |

[a]Stimulant for ThS: 10 μg/ml S—Ag.

Production of IL-2 activity was measured in ThS cultures stimulated with antigen, and in EL-4 cultures stimulated with PMA, as shown in Table 2. Net background production of IL-2 by unstimulated ThS and unstimulated EL-4 cells was low. The antigen-stimulated ThS cells also produced IL-3 (cf. Table 3). A reduced number of producer cells per well resulted in a lowered IL-3 activity. The WEHI cell line produced high levels of IL-3 constitutively, as expected, (cf. Lee et al., 1982, *J. Immunol.* 126, 2184).

GENERAL PROPERTIES AND APPLICATIONS OF THE INVENTION—SUMMARY

As shown in Tables 2 and 3, the assay system of the present invention requires a minimal number of producer cells for an easily measurable release of soluble mediator. This system could be used for detection of either growth-stimulatory or growth-inhibitory activity. Assaying of the activity concomitant with its production without the use of a semipermeable dividing membrane allows the detection of labile mediators, while eliminating the doubt inherent in other one-step assays, particularly the danger that the putative factor might bind to the membrane. By the same token, plating the inhibiting and the inhibited cells in the same well, in parallel to plating them in opposite connected wells, with inhibition apparent only in the former case, will directly show the presence of contact-mediated inhibition rather than inhibition mediated by a soluble product (Table 1). Thus, the present invention can be used not only to show the presence of a soluble mediator such as hormones, but also the presence of a non-soluble mediator of inhibition or of enhancement.

The method and apparatus of the present invention also can be used for measuring metabolic activity by protein synthesis, using a $C^{14}$-amino acid, such as leucin, as a marker. The cells are grown, harvested, and counted in a counter for a determination of how much protein is produced. Alternatively, $^3$H-uridine uptake can be measured for determining RNA synthesis.

The results of the assay according to the present invention can be available in less than 48 hours (depending on the system). Therefore, it is envisioned that the assay may be useful for screening of cultures where time is of particular importance, such as in the case of newly cloned T-cell hybridomas. There is also the advantage of being able simultaneously to follow the status of the producer cultures during the assay. It can be seen from Table 2 that a dramatic inhibition of the proliferation of EL-4 cells is apparent in the presence of PMA, and is reciprocal to the production of IL-2 activity by this cell line.

DETAILED DESCRIPTION OF THE DRAWINGS

FIG. 1 shows a microculture tray 10 comprising a base plate 13 having therein a plurality of pairs of wells 11, each pair of which are connected by troughs 12 which extend downwardly about ⅔ of the depth of the well from the top.

FIG. 2 is a copy of a photograph showing that cells did not pass from one well 20 into an adjacent unseeded well 21.

In order to prepare a tray according to the present invention, adjacent wells of a standard 96-well microculture tray (Falcon, Oxnard Calif., or Costar, Cambridge, Mass.) were connected by melting through the dividing wall at the point of contact, down to about ⅓ the depth of the well from the bottom, using a blunt-tip metal spatula heated over a flame. Molten paraffin wax (Paraplast Plus pellets, Sherwood Medical Industries, St. Louis, Mo.) was pipetted into the interwell spaces outside the wells other than the troughs to prevent leakage of medium sideways. The entire procedure was preformed in a laminar flow hood to ensure sterility.

The cells were distributed into the wells to give a total volume of 0.2 ml, using a multichannel pipetting device (Eppendorf) and the trays were placed in a 37° C. incubator for 1-2 hours to allow the cells to settle. The supernatants of the adjacent cultures were then connected by passing a hypodermic needle through the trough openings between the wells and connecting each well to the corresponding trough. Stimulants, if any, can be added to the wells in a volume of 10 microliters. After a 24-48 hour incubation, the cultures were labelled overnight with 1 microcurie $^3$H-thymidine/well, harvested with an automatic cell harvester (Mash 2, M. A. Bioproducts, Walkersville, Md.) and counted by standard liquid scintillation.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

What is claimed is:

1. A microculture tray for the rapid detection of migration from a first well onto a second well of a soluble or non-soluble in situ-produced mediator, comprising a base plate having a top and a bottom portions;
at least one pair of separate wells having a preset depth consisting of a first and a second well extending downwardly from the top portion to the bottom portion of the base plate, the separate wells being separated from one another by interwell spaces; and at least one means for allowing free passage of supernatant but not of cells settled in the bottom portion of the wells between first well and the second well, said means connecting the separate wells of the pair of wells, said means extending downwardly from the top of the base plate about $\frac{2}{3}$ of the depth of the connected wells.

2. A microculture tray for the rapid detection of migration from a first well onto a second well of a soluble or non-soluble in situ-produced mediator, comprising a base plate having a top and a bottom portions;

at least one pair of separate wells having a preset depth consisting of a first and a second well extending downwardly from the top portion to the bottom portion of the base plate, the separate wells being separated from one another by interwell spaces; and at least one trough connecting the separate wells of the pair of wells, the trough extending downwardly from the top of the base plate about $\frac{2}{3}$ of the depth of the connected wells to allow free passage of supernatant but not of cells settled in the bottom portion of the wells between the first well, the trough and the second well.

3. The tray of claim 2, wherein the tray is made of a hydrophobic material.

4. The tray of claim 2, wherein the interwell spaces are filled with paraffin.

5. The microculture tray of claim 2 comprising a plurality of pairs of wells.

6. The microculture tray of claim 5 being a 96-well microculture tray.

* * * * *